United States Patent [19]

Howe

[11] 4,420,679

[45] Dec. 13, 1983

[54] GAS CHROMATOGRAPHIC OVEN USING SYMMETRICAL FLOW OF PREHEATED - PREMIXED AMBIENT AIR

[75] Inventor: Robert L. Howe, San Ramon, Calif.

[73] Assignee: Delta Associates, Inc., San Jose, Calif.

[21] Appl. No.: 352,656

[22] Filed: Feb. 26, 1982

[51] Int. Cl.³ .................. B01D 15/08; H05B 1/02; F27D 7/04
[52] U.S. Cl. .................. 219/400; 73/23.1; 126/21 A; 99/476; 219/386; 219/413
[58] Field of Search ............ 219/400, 386, 387, 413; 432/178, 179; 34/209, 227, 219–225, 235; 99/473–476; 126/21 A, 21 R; 422/70, 89; 73/23.1

[56] References Cited

U.S. PATENT DOCUMENTS

| | | | |
|---|---|---|---|
| 2,499,525 | 3/1950 | Person | 126/21 A |
| 2,957,067 | 10/1960 | Scofield | 126/21 A |
| 3,165,147 | 1/1965 | Roof | 73/23.1 |
| 4,050,911 | 9/1977 | Welsh | 73/23.1 |
| 4,051,347 | 9/1977 | Röhrl | 126/21 A |
| 4,181,613 | 1/1980 | Welsh | 73/23.1 |
| 4,186,295 | 1/1980 | Iwao | 219/400 |

OTHER PUBLICATIONS

Hewlett–Packard Technical Paper GC–68, "Evaluation of Commercial Gas Chromatograph Ovens", Paul Welsh, Aug. 1977.

Primary Examiner—B. A. Reynolds
Assistant Examiner—Teresa J. Walberg
Attorney, Agent, or Firm—Thomas E. Schatzel

[57] ABSTRACT

A temperature controlled oven apparatus having a central chamber with a heater element and a pivotal inner baffle door, located within a removable outer access door, periodically opened or closed to regulate the exhaust of oven air and the admission of ambient air into the oven through a preheated plenum chamber.

7 Claims, 3 Drawing Figures

U.S. Patent  Dec. 13, 1983  Sheet 1 of 2  4,420,679
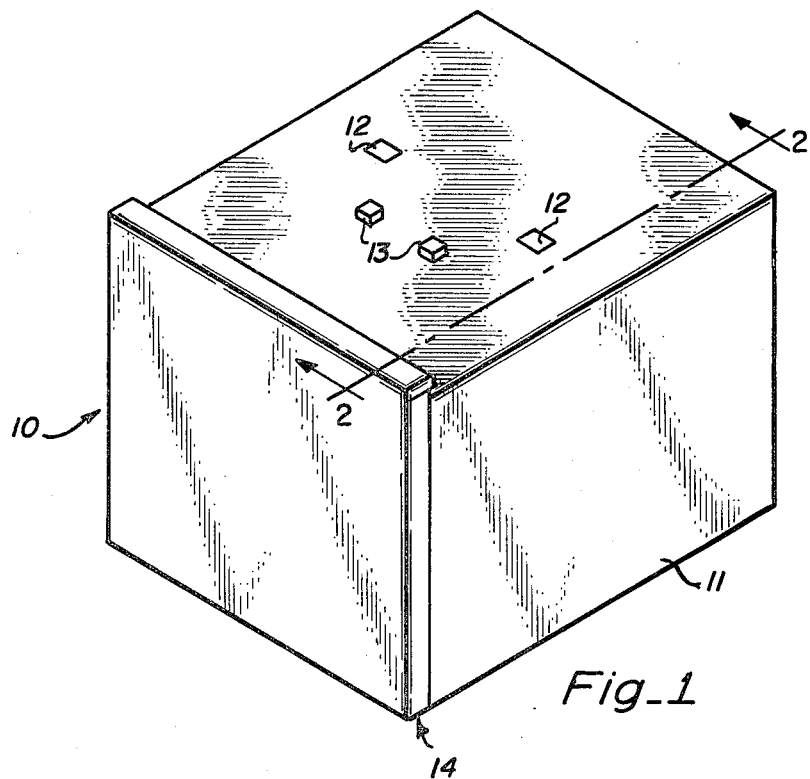
Fig_1
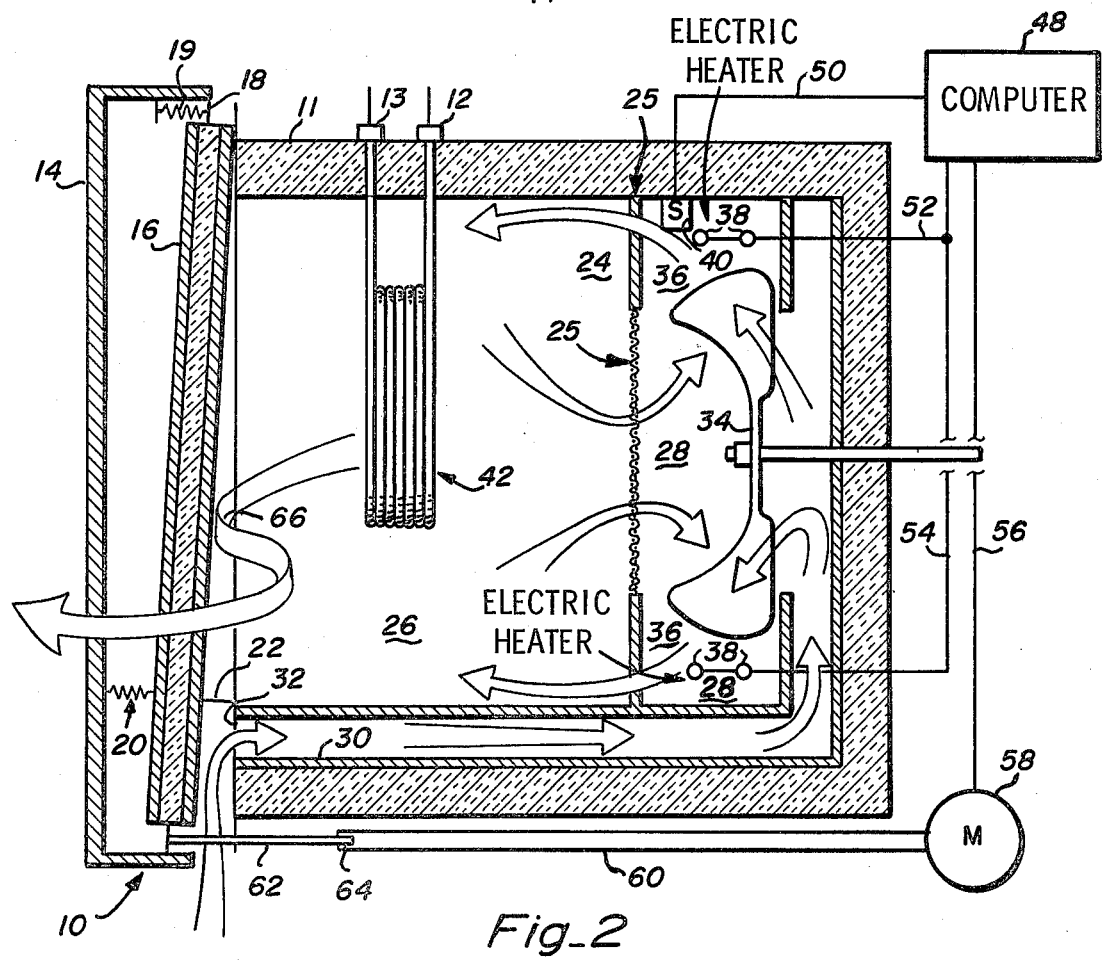
Fig_2

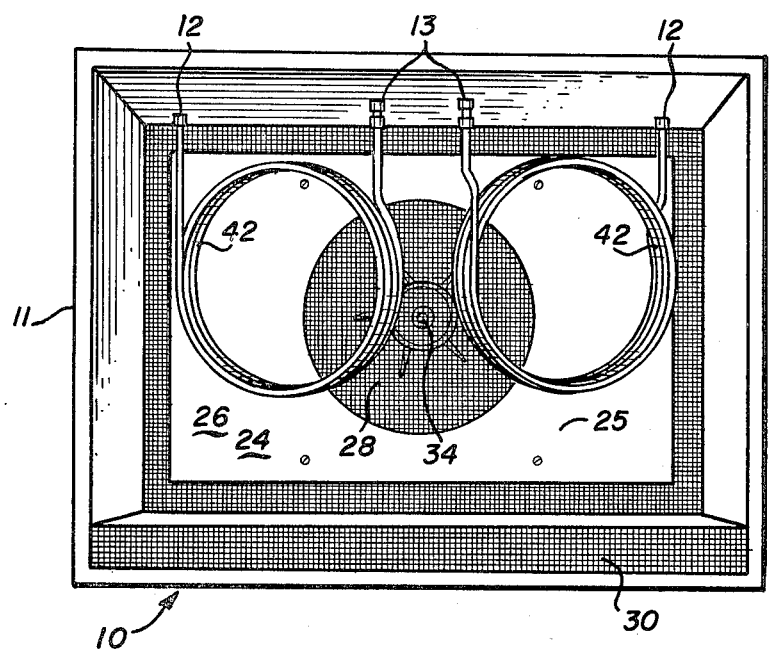
Fig_3

GAS CHROMATOGRAPHIC OVEN USING SYMMETRICAL FLOW OF PREHEATED - PREMIXED AMBIENT AIR

BACKGROUND OF THE INVENTION

1. Field of the Invention

The present invention relates generally to gas chromatographic separation and more particularly to an improved instrument oven for gas chromatography separation wherein the air replenishment system permits the oven to operate at near ambient temperatures with minimal temperature gradients.

2. Description of the Prior Art

In the field of gas chromatography separation, sample test apparatus is operated in a temperature controlled oven. A column, usually a long glass tube wound in a circular fashion, packed with coated particles, is a component of the test apparatus suspended in the oven between a sample injector and a sample detector. When a sample is injected, it travels through the column packing until it reaches the detector. Because the time that the sample is in residence or retained within the column packing is indicative of the characteristic identification of the sample, the physical conditions of the column should be repeated for each test run. Therefore, a purpose of the oven is to attempt to provide the same operating temperatures for each test run.

For a gas chromatographic oven to achieve its intended purpose, the oven temperature must be accurately controlled with a minimum of temperature variations. As previously noted, the columns are usually glass and temperature variations will cause the temperature along the columns to vary. Since the sample must be exposed to a homogeneous temperature throughout the column packing to control its retention time and to prevent sample decomposition and other problems, temperature variations or gradients continue to be a persistent problem. Also, there must be a controlled temperature program that is reproducable from one test run to the next to ensure repeatable retention times. The oven must also operate as near to ambient temperature as possible in order to retain samples having low boiling points. This requirement is difficult to satisfy because the injector and detector test apparatus projecting down into the heated oven operate at several hundred degrees centigrade. The oven must also have a large internal volume to accommodate the test apparatus and also be capable of cooling down rapidly from high temperatures to prepare for the next test run.

In the prior art, external air was introduced into the oven when it is operated near ambient temperature to counteract the external heat inputs from the test apparatus. In one attempt, the external air is induced directly into the oven through an opening in the oven door creating high temperature gradients because the cooler ambient air passed directly over the column without any preheating. In a second attempt, the oven door was opened to ambient permitting air to enter and leave randomly around the door edges. This method also leads to high temperature gradients because the cooler air was drawn directly into the oven and the open door served to interface with aisleway traffic. A third attempt utilized a method of premixing the ambient air prior to entering the oven chamber. In particular, one damper controlled the air admitted into the chamber from behind the fan and a second adjacent damper controlled the air expelled from the chamber. Because the two damper openings were adjacent to one another, the flow was unsymmetrical resulting in a short circuiting of the air circulation path. Moreover, two additional openings were required in the oven housing.

Prior to the present invention, Paul Welsh in Hewlett-Packard Company Technical Papers No. GC-67 and GC-68 entitled "The Evaluation and Use of Gas Chromatograph Inspection Ports" and "Evaluation of Commercial Gas Chromatograph Ovens", respectively, explained that high temperature gradients about the test column continued to exist. The result was non-repeatable retention times and sample decomposition such that test runs were difficult to identify and compare.

SUMMARY OF THE PRESENT INVENTION

It is therefore an object of the present invention to provide an accurately controlled temperature at near ambient temperatures with minimal temperature gradients within the oven.

It is a further object to provide a temperature program that is reproducable from the first sample test to the last.

It is a further object to provide an oven with a sufficient volume to accomodate four test columns.

Briefly, in a preferred embodiment, the present invention includes a thermally insulated housing, a central chamber comprised of an anterior chamber and a posterior chamber, an outer access door, an inner baffle door, a computer-controlled actuator and heater, a plenum chamber, an electric fan, a temperature sensor, an air intake and exhaust path, and at least one test column apparatus. Generally, the oven air is constantly monitored by a sensor which transmits temperature data to a computer for comparison to a programmed temperature set point. Also, the electric power supplied to the heater is monitored and the results of this comparison and monitoring determine computer action.

If heat is required, the inner baffle door is closed and heater power is increased. If cooling is required, heater power is reduced and the inner baffle door is opened permitting oven air to exhaust and ambient air to enter the plenum chamber to be preheated, premixed with oven air, and then symmetrically distributed to maintain the preset temperature and reduce temperature differentials. Thus, cool air is never drawn directly into the oven, minimizing the potential for temperature gradients about the test column.

An advantage of the gas chromatographic oven of the present invention is that the temperature is accurately controlled at near ambient temperatures with minimal temperature gradients within the oven resulting in reproducible retention times of samples within the test columns.

Another advantage is that the program temperature is reproducible from the first sample test to the last providing test results which are comparable.

A further advantage is that the oven has a sufficient volume to accomodate parallel square mounting limited to four test columns.

These and other objects and advantages of the present invention will no doubt become obvious to those of ordinary skill in the art after having read the following detailed description of the preferred embodiment which is illustrated in the various drawing figures.

IN THE DRAWING

FIG. 1 is a perspective view of a gas chromatography oven in accordance with the present invention;

FIG. 2 is a cross-sectional view of the gas chromatography oven taken along the line 2—2 of FIG. 1; and FIG. 3 is a frontal elevation view of the gas chromatography oven of FIG. 1 with the outer access door removed.

DESCRIPTION OF THE PREFERRED EMBODIMENT

FIG. 1, illustrates a gas chromatographic oven referred to by the general reference numeral 10 and incorporating the present invention. The oven 10 includes a thermally insulated housing 11 with a sample injector 12; a sample detector 13, and a removable outer access door 14.

FIG. 2 illustrates a cross-sectional view of oven 10 and also displays housing 11, injector 12, detector 13 and outer access door 14. Note that an inner baffle door 16 is pivotally attached to outer access door 14 at a pivot point 18 and is under a compression sealing spring 19 and a compression spring 20. Also, a partition 22 is physically attached to the inner baffle door 16. Within housing 11 there exists a central chamber 24 compartmentized by a chamber divider 25 and forming an anterior chamber 26 and a posterior chamber 28. Located intermediate housing 11 and central chamber 24 is a plenum chamber 30 which carries air from an intake 32 to an electric driven fan 34 and then past a premixing area 36, an electric heater 38, and a temperature sensor 40, all respectively located within posterior chamber 28. Within anterior chamber 26 there exists a chromatographic test column 42 with sample injector 12 and sample detector 13 mounted atop insulated housing 11. Sensor 40 is electrically connected to a computer 48 by a sensor line 50 and heater 38 is electrically connected to computer 48 by a heater lines 52 and 54. In addition, computer 48 is electrically connected by a line 56 to a stepper motor 58 which physically drives an actuator shaft 60 which in turn operates an activator pin 62 through a treaded joint 64. Finally, pin 62 contacts inner baffle door 16 to create oven exhaust path 66.

At the beginning of sample testing, oven 10 is often at or very near ambient temperature and it is at this stage that temperature gradients about the test column 42 will cause the retention times of the samples to vary. To combat this problem, sensor 40 within housing 11 is so disposed as to monitor the air movement traversing column 42. As many as four test columns 42 can be simultaneously placed within anterior chamber 26. However, only one test column 42 is illustrated in FIG. 1 for clarity and discussion purposes. As previously noted, sensor 40 is electrically connected to computer 48 via line 50. It is the temperature data sent by sensor 40 on line 50 that directs the operation of computer 48. Each sample run must begin with a constant column temperature to repeat the sample retention time, that is, the characteristic residence time that a particular sample takes to travel through a particular column. This residence time can then be used to identify that sample. Any temperature variations existing within the anterior chamber 26 will be reported to computer 48 and a programmed sequence will follow. In order to minimize temperature differentials, a change in heat and/or a change in preheated, premixed ambient air flow is required. Note heater 38, which is always energized to a minimum power control level, can be controlled by computer 48 to provide additional heat to the air of the central chamber 24. Also, computer 48 can operate stepper motor 58 to position inner baffle door 16 such that intake path 32 and exhaust path 66 are exposed to ambient air. Additionally, computer 48 can perform both functions simultaneously. It is the constant monitoring of the air delivered to test column 42 by sensor 40 that controls the power delivered to heater 38 and the position of inner baffle door 16 by computer 48. This method permits the most efficient operation by minimizing the power to the heater 38, thus minimizing temperature gradients within anterior chamber 26.

A sample to be measured enters the test column 42 via sample injector 12 and exits through sample detector 13. Because reproducible retention times of samples depends upon reproducible temperatures of the column 42, sensor 40 continuously monitors the air temperature delivered to column 42. When sensor 40 signals computer 48 that additional heat is required to meet the program sequence, computer 48 increases the power transmitted to heater 38 over lines 52 and 54. Also, the inner baffle door 16 will be closed if power to heater 38 is greater than a minimum preset value. In this manner, additional heat is provided to anterior chamber 26 until updated air temperature data about column 42 is transmitted to computer 48 by sensor 40. This updated temperature data controls the rate of power delivered to heater 38 and also operates to reduce temperature variations about column 42.

When sensor 40 signals computer 48 that the air temperature about column 42 in anterior chamber 26 is too high, the computer 48 then compares the data of sensor 40 with the program data of computer 48 to determine how far the temperature of oven 10 should be reduced. The computer 48 then sends a signal via lines 52 and 54 to reduce power to heater 38 and if the power to heater 38 is below a preset value, computer 48 also sends an electrical signal to the controller of stepper motor 58 via line 56. Note that motor 58 is not a continuous duty device and only operates while the signal on line 56 is present. After stepper motor 56 is energized, it imparts rotational motion to actuator shaft 60 which is connected to actuator pin 62 via threaded joint 64. Thus, when shaft 60 is rotated by motor 58, pin 62 is advanced forward or backwards with the rotation of shaft 60 about threaded joint 64. Thus, the rotational motion of motor 58 is converted to translation motion in pin 62 which physically contacts the bottom of inner baffle door 16. Also, sufficient pressure must be applied to inner baffle door 16 to overcome compression spring 20. Therefore, temperature data of sensor 40 is used to rotate the inner baffle door 16 about pivot point 18. It is the computer 48 program control of motor 58 that controls when the inner baffle door 16 is operated and how far the door 16 is pivoted open or closed about hinge 18 and against compression spring 20. This action is accomplished by the constant monitoring by computer 48 of the electric power supplied to heater 38 in comparison with a minimum power control level. Because the program of computer 48 seeks to minimize the power utilized, inner baffle door 16 is periodically repositioned to maintain the power to heater 38 at a minimum level.

When inner baffle door 16 is pivoted open about pivot point 18, intake path 32 and exhaust path 66 are exposed to ambient air through the bottom and sides of outer access door 14. Because electric fan 34 is continuously operating, a negative pressure is experienced in plenum chamber 30 when the inner baffle door 16 is open. Thus, ambient intake air is drawn into plenum chamber 30 and travels toward fan 34. Note that plenum chamber 30 is located intermediate insulated housing 11 and central chamber 24 and it is at this point that the preheating of the intake air takes place. The metal floor of central chamber 24 passes heat to the incoming ambient air in a heat exchanger fashion by convection and radiation. Then the preheated air is drawn past fan 34 and commingled in premixing area 36 with air drawn into fan 34 from anterior chamber 26. After preheating and premixing, the fan 34 distributes the air past heater 38 and sensor 40 and then through the outer screen of chamber divider 25 in a centrifugal pattern.

This air replaces hotter air of anterior chamber 26 that either exits oven 10 via exhaust path 66 or is drawn into premixing area 36 through the center screen of chamber divider 25 by fan 34. As the replacement air travels past sensor 40, continuous data is transmitted to computer 48 so that heaters 38 and inner baffle door 16 may be operated as required to minimize power and to maintain the preset temperature of oven 10. Isothermal gradients about column 42 are minimized because cooler ambient air is never drawn directly into oven 10 while operating at low temperatures. Since the power to heater 38 is minimized, this reduces the required volume of cooler air drawn by intake 32. Thus, the retention times become reproducible and samples become more identifiable.

The prior art attempts to solve this problem did not incorporate premixing and preheating and the one attempt at a premixing design required two additional openings in the housing resulting in an asymetrical air flow. The instant invention reduces the asymetrical air flow by drawing air into a single preheated inlet, premixing and then distributing the air in a uniform pattern prior to exhausting the air at the opposite end of the oven 10.

FIG. 3 illustrates a frontal view of oven 10 with outer access door 14 removed and anterior chamber 26 exposed. Note that plenum chamber 30 appears between central chamber 24 and housing 11. Also, note that chamber divider 25 separates the central chamber 24 into anterior chamber 26 and posterior chamber 28. Two test columns 42, a portion of sample injectors 12, and a portion of sample detectors 13 are mounted in the housing 11 and extending down into anterior chamber 26. Fan 34 appears in posterior chamber 28 behind chamber divider 25. Note the center and outer screens of chamber divider 25 permit the air from fan 34 to be distributed in a symetrical manner. Also note that oven 10 exhibits an advanced design of the columns 42 which permits parallel square mounting limited to four columns 42.

Although the present invention has been described in terms of the presently preferred embodiment, it is to be understood that such disclosure is not to be interpreted as limiting. Various alterations and modifications will no doubt become apparent to those skilled in the art after having read the above disclosure. Accordingly, it is intended that the appended claims be interpreted as covering any alterations and modifications as fall within the true spirit and scope of the invention.

I claim:

1. Apparatus for operating a gas chromatographic oven at near ambient temperature with minimal temperature gradients, comprising in combination:
    a housing means with an outer access door and a central chamber consisting of an anterior chamber for providing a heated environment for chromatographic test apparatus and a posterior chamber for minimizing thermal gradients by providing a homogeneous oven temperature about said test apparatus;
    insulation means located within the walls of the housing means for providing a thermal boundary between said central chamber and the ambient environment;
    plenum chamber means positioned between said central chamber and the housing means for preheating intake air prior to introduction of said air into said central chamber to eliminate temperature differentials in said central chamber;
    adjustable inner baffle means positioned between the housing means and said outer access door for regulating the flow of said intake air to the plenum chamber and exhaust air from said anterior chamber;
    partition means connected to the inner baffle means for isolating said intake air to the plenum chamber from exhaust air of said anterior chamber;
    actuator means located outside the housing means and in mechanical communication with the inner baffle means for positioning the inner baffle means;
    air distribution means positioned within said posterior chamber for premixing said intake air with existing central chamber air and distributing said premixed air to said anterior chamber;
    heater means positioned within said posterior chamber for heating said premixed air to a program temperature to minimize oven thermal gradients;
    sensor means positioned within said posterior chamber of the housing means for sensing the temperature within said central chamber; and
    an automatic control means connected to said actuator means and said heater means for receiving temperature data from said sensor means and for transmitting control signals to said heater and actuator means in response to temperature.

2. The apparatus of claim 1 further including a spring pivot means for connecting the inner baffle means to said outer access door, whereby the inner baffle means may be rotated about said spring pivot means by the translational motion of said actuator.

3. The apparatus of claim 1 further including a compression spring positioned between said outer access door and the inner baffle means for sealing the inner baffle means when said actuator is withdrawn.

4. The apparatus of claim 1 wherein said outer access door is removable to increase access to said test apparatus.

5. The apparatus of claim 1 wherein said automatic control means comprises a computer programmed to drive a stepper motor and energize said heater means responsive to oven sensor data supplied to said computer.

6. The apparatus of claim 1 wherein said heater means comprises a temperature controlled electric filament.

7. The apparatus of claim 1 wherein said air distribution means comprises an electrical driven fan for premixing and distributing said preheated intake air with existing central chamber air.

* * * * *